United States Patent [19]

Stait et al.

[11] 4,030,496
[45] June 21, 1977

[54] SYRINGE FOR INJECTING LIQUIDS INTO BLOOD VESSELS OF LIVING BODIES

[75] Inventors: Donald Peter Stait, Steinmaur; Willi Zenger, Zurich, both of Switzerland

[73] Assignee: Contraves AG, Zurich, Switzerland

[22] Filed: July 12, 1976

[21] Appl. No.: 703,898

[30] Foreign Application Priority Data

July 28, 1975 Switzerland .................... 9799/75

[52] U.S. Cl. .......................... 128/215; 128/218 P; 128/234
[51] Int. Cl.² ........................................ A61M 5/00
[58] Field of Search .......... 128/215, 214, 216, 217, 128/218 R, 218 P, 218 PA, 219, 220, 234; 92/172, 248, 249, 181, 245

[56] References Cited

UNITED STATES PATENTS

| 449,883 | 4/1891 | Molinari | 128/219 |
|---|---|---|---|
| 3,581,956 | 6/1971 | Reid | 128/218 P X |

FOREIGN PATENTS OR APPLICATIONS

| 1,104,570 | 6/1955 | France | 128/218 P |
| 1,108,413 | 1/1956 | France | 128/218 P |

*Primary Examiner*—John D. Yasko
*Attorney, Agent, or Firm*—Werner W. Kleeman

[57] ABSTRACT

A syringe for injecting liquids into blood vessels of living bodies comprising a cylinder equipped at one end with an attachment flange and at the other end with a catheter connection. A piston insertable into the cylinder and having a sealing ring arranged in a groove. Between the sealing ring and the inner wall of the cylinder there is arranged a substantially L-shaped slide ring operatively connected with the piston. This slide ring sealing bears by means of a first leg at the inner wall of the cylinder and by means of a second leg in a channel or recess which is parallel to the aforesaid groove. A substantially cylindrical shoulder extending from the channel up to an inclined portion of the tip of the piston extends at least to the center or center line of the deformed sealing ring.

5 Claims, 3 Drawing Figures

SYRINGE FOR INJECTING LIQUIDS INTO BLOOD VESSELS OF LIVING BODIES

BACKGROUND OF THE INVENTION

The present invention relates to a new and improved construction of syringe for injecting liquids into blood vessels of living bodies which is of the type comprising a cylinder provided at one end with an attachment flange and at the other end with a catheter connection, a piston is introducable into the cylinder and has an elastic rubber sealing ring arranged in a groove.

In German patent publication No. 1,566,585, there is disclosed an injection device for x-ray contrast agents wherein there is taught a syringe having a to-and-fro movable piston which in conventional and therefore non-illustrated manner is provided with the required sealing ring arranged in a groove. In the assembled condition of the device such sealing ring is pressed against the inner wall of the cylinder. This seal has the drawback that due to the wall friction which prevails, upon actuation of the piston, between the deformed sealing ring and the inner wall of the cylinder and which friction only can be overcome with difficulty, there can not be guaranteed for faultless operation of the entire injection device — piston advance speed with respect to the adjusted liquid conveying.

Furthermore, there is known to the art a syringe from German patent publication No. 2,314,949 which possesses a piston movable to-and-fro in a cylinder of the syringe, the piston having a one-piece rubber seal which surrounds the front portion of the piston first in a convex form and thereafter in a cylindrical form. The cylindrical configured portion of the seal has an inwardly directed ring-bead which engages in a groove provided at the piston and a further, but this time outwardly directed ring-bead which extends towards the inner wall of the cylinder and serves as a seal. The drawback of this syringe resides in the fact that the sealing edge formed by the ring-bead directed towards the inner wall is located at a relatively large distance from the front edge — transition from the convex shape to the cylindrical shape — and in this relatively narrow ring gap there are entrapped air bubbles which are difficult if not in fact impossible to eliminate. Additionally, the field of application of this syringe is markedly limited due to the rubber seal.

In German patent publication No. 2,061,802 there is taught a syringe having a piston which can move to-and-fro or reciprocate within a cylinder, this piston being provided at its front portion with a conical surface. Arranged in the piston is a mandrel provided with threading and possesses a head portion or piece provided with a conically configured surface at the side confronting the conical surface of the piston. The head portion with its conical surface is correspondingly arranged with respect to the conical surface of the piston, so that both surfaces collectively form an endless groove for a sealing O-ring held in position by a sleeve surrounding the head portion of the mandrel as well as part of the piston. By suitably rotating the mandrel in the piston both of the conical surfaces are drawn towards one another, so that the groove is reduced in size, and hence, the sealing O-ring is outwardly elongated, with the result that the sleeve at this location sealing presses against the cylinder wall. Also this syringe is associated with the disadvantage that the location serving as the seal is oriented relatively far from the front edge of the sleeve, and thus, there is formed a narrow ring-shaped gap between the cylinder wall and the sleeve within which there become entrapped air bubbles which are difficult or impossible to remove and are extremely dangerous for the patient undergoing treatment.

SUMMARY OF THE INVENTION

Hence, it is a primary object of the present invention to provide an improved construction of syringe for injecting liquids into the blood vessels of living bodies which is not associated with the aforementioned drawbacks and limitations of the prior art proposals.

Another and more specific object of the present invention is directed to the provision of a syringe having a seal arrangement for a piston which can reciprocate in a cylinder, which possesses both optimum sliding- and sealing properties, also possesses at the side confronting the medium, between the cylinder inner wall and the piston, a ring-shaped surface of minimum dimension and devoid of any gaps and cutouts.

Now in order to implement these and still further objects of the invention which will become more readily apparent as the description proceeds, the new and improved syringe of this development is manifested by the features that a substantially L-shaped slide or sliding ring which is operatively connected with the piston is arranged between the sealing ring and the cylinder inner wall, this L-shaped slide ring sealing bearing with a first leg at the inner wall and is inserted by means of a second leg in a channel or recess extending parallel to the groove for the sealing ring. Further, a cylindrical shoulder which extends from the groove of the sealing ring to the inclined portion of the tip of the piston extends at least up to the center of the deformed sealing ring.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE INVENTON

Figure 1:
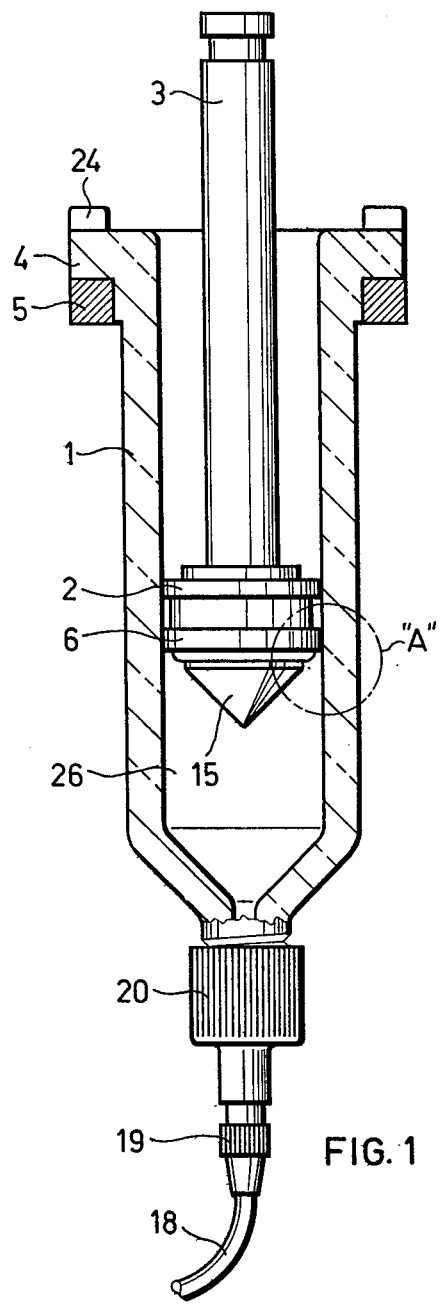
FIG. 1 illustrates a syringe constructed according to the invention, partly in section, with the connected catheter.

Describing now the drawings in FIG. 1 there is illustrated in partial sectional view a cylinder 1 within which there is reciprocally guided a piston 2 which can be actuated by a not particularly illustrated injector, this piston 2 being provided with a piston rod 3.

At one end of the cylinder 1 there is provided a flange 4, a ring 5 located behind the flange as well as two tightening cams or elements 24 at the end face. The cylinder 1 along with the parts 4 and 5 can be inserted so as to be self-centered into a recess provided at the injector, and the cams 24 act against appropriately arranged springs so that the injector and the cylinder 1, when assembled, for a stable unit.

Figure 3:
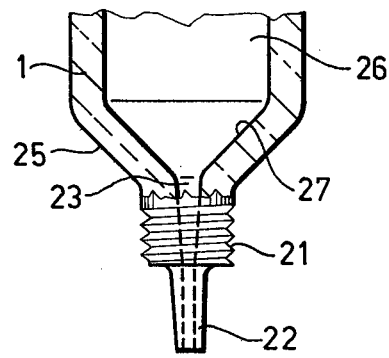
FIG. 3 is a fragmentary sectional view of the connection portion for the catheter of the syringe shown in FIG. 1.

In FIG. 3 there is ilustrated the other end of the cylinder 1 and it will be recognized such has a substantially conical configuration and is provided with a threaded portion 21 merging with the outer surface or wall 25 of the cylinder as well as a tip 22 formed at the threaded portion 21. The likewise conical-shaped inner wall 27 communicates with a continuous bore 23 which extends to the front end of the tip 22, the bore 23 having a slightly conical configuration at the region of the threaded portion 21 and possesses an essentially cylindrical configuration at the region of the tip 22.

The threaded portion 21 serves to receive a retaining nut or screw cap 20 with the aid of which there can be drawn and sealingly connected at the tip 22 a catheter 18 having a connection portion 19 and which has been slipped onto the tip 22, as best seen by referring to FIG. 1.

The cylinder 1 is preferably fabricated by injection molding a transparent plastic, such as for instance polysufone, polycarbonate or the like, however the possibility exists of also forming the cylinder of a suitable metal.

Figure 2:
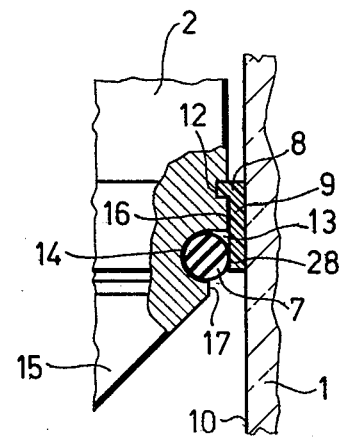
FIG. 2 illustrates on an enlarged scale, in sectional view, the portion of the syringe designated by reference character "A" in FIG. 1.

In FIG. 2 there is shown on an enlarged scale the sealing arrangement for the piston 2 at the region of the cylinder inner wall 10. In an endless channel or groove 12 provided at the piston 2 there is secured a substantially L-shaped slide or bearing ring 6 which has been inserted upon the piston 2, the shorter leg 8 of the slide ring 6 being secured in the channel 12 and the longer leg 9 sealing bearing against the inner wall 10 of the cylinder 1.

The slide ring 6 is likewise preferably formed by injection molding an elastic material having good sliding properties, such as for instance "TEFLON", polyamide or the like.

According to a modified version of the slide ring the leg 8 is designed larger than such leg as illustrated in FIG. 2, is slotted at its periphery and subdivided into a number of sections. With this construction the leg 8 is inserted over the piston with the individual segments spread apart, and subsequently engages with the channel 12 which in this case is somewhat deeper.

At the front region of the piston 2 there is arranged a groove 14 into which there is inserted a sealing ring 7 formed of an elastomer capable of withstanding high temperatures. The one side of the sealing ring 7 presses the leg 9 against the inner wall 10 of the cylinder 1 and the other side thereof sealing bears in the groove 14.

The leg 9 of the slide or sliding ring 6, in the assembled condition of the syringe and with the sealing ring 7 deformed, extends at least up to the center however not further than the surface 28 of the sealing ring 7 which in this position bears at the leg 9. Moreover, a hollow space or compartment 13 at the side of the sealing ring 7 facing away from the medium or injectate and formed between the leg 9, a shoulder 16 and the sealing ring 7 is filled with a suitable rubber mass, such as for instance "SILASTIC" (heat stable silicone) "BOSTIK" or the like.

The piston 2 is constructed at the side impinged by the medium preferably as a circular-shaped conical tip 15 and following such possesses a therewith merging substantially cylindrical shoulder 17 extending to the groove 14. In order to prevent the sealing ring 7 from falling out of the groove 14 and to prevent the adherence of bubbles at such region, the diameter of the shoulder 17 extends to the center, preferably however somewhat past the center or center line of the sealing ring 7, however the diameter is in no event to be chosen so large that there is formed a gap between the shoulder 17 and the sealing ring 7.

While there are shown and described present preferred embodiments of the invention, it is to be distinctly understood that the invention is not limited thereto, but may be otherwise variously embodied and practiced within the scope of the following claims.

Accordingly, what is claimed is:

1. A syringe for injecting liquids into blood vessels of living bodies, comprising a cylinder having opposed ends, one end of the cylinder being provided with a flange and the other end of the cylinder being provided with a catheter connection, a piston arranged for two-and-fro movement in the cylinder, said piston having a groove, a sealing ring arranged in said groove, said piston having a channel which is substantially parallel to said groove, a substantially L-shaped slide ring arranged between the sealing ring and an inner wall of the cylinder, said L-shaped slide ring having a first leg and a second leg, the first leg sealing bearing against the inner wall of the cylinder, said second leg being inserted in said channel to operatively connect the slide ring with piston, said piston including an inclined portion extending to a tip of the piston, said piston having a substantially cylindrical shoulder extending from said groove to the start of the inclined portion of the piston tip, said cylindrical shoulder extending at least to the region of the center of the deformed sealing ring.

2. The syringe as defined in claim 1, wherein the first leg of the slide ring in the assembled condition extends at least to the center of a surface of the deformed sealing ring bearing at said first leg but not beyond such surface.

3. The syringe as defined in claim 1, wherein the cylindrical shoulder extending to the region of the center of the deformed sealing ring is not greater in diameter than the side surface of the deformed sealing ring bearing in the groove.

4. The syringe as defined in claim 1, wherein the piston includes a shouler portion against which bears the L-shaped sliding ring, said shoulder portion, the sealing ring and the slide ring forming a compartment filled with a rubber mass.

5. A syringe for injecting liquids into blood vessels of living bodies, comprising a cylinder, a piston arranged for two-and-fro movement in the cylinder, said piston having a groove, a sealing ring arranged in said groove, said piston having a channel, a substantially L-shaped slide ring arranged between the sealing ring and an inner wall of the cylinder, said L-shaped slide ring having a first leg and a second leg, the first leg sealing bearing against the iner wall of the cylinder, said second leg being inserted in said channel to connect the slide ring with the piston, said piston including an inclined portion, said piston having a substantially cylindrical shoulder extending from said groove to the start of the inclined portion of the piston tip, said cylindrical shoulder extending at least to the center of the deformed sealing ring.

* * * * *